(12) United States Patent
Pellinen et al.

(10) Patent No.: US 10,118,030 B2
(45) Date of Patent: Nov. 6, 2018

(54) OMNIDIRECTIONAL DEPLOYABLE MULTICHANNEL NEURAL ELECTRODE SYSTEM

(71) Applicant: NeuroNexus Technologies, Inc., Ann Arbor, MI (US)

(72) Inventors: David S. Pellinen, Ann Arbor, MI (US); Bencharong Suwarato, Ann Arbor, MI (US); Rio J. Vetter, Van Buren Township, MI (US); Jamille Farraye Hetke, Brooklyn, MI (US); Daryl R. Kipke, Dexter, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 797 days.

(21) Appl. No.: 14/519,346

(22) Filed: Oct. 21, 2014

(65) Prior Publication Data
US 2015/0112360 A1 Apr. 23, 2015

Related U.S. Application Data

(60) Provisional application No. 61/893,603, filed on Oct. 21, 2013, provisional application No. 61/895,109, filed on Oct. 24, 2013.

(51) Int. Cl.
*A61B 19/00* (2006.01)
*A61N 1/05* (2006.01)
(Continued)

(52) U.S. Cl.
CPC ........ *A61N 1/0558* (2013.01); *A61B 5/04001* (2013.01); *A61B 5/0478* (2013.01);
(Continued)

(58) Field of Classification Search
CPC ................ A61N 1/0558; A61N 1/0534; A61N 1/36017; A61B 5/0478; A61M 25/007; A61M 25/003; G03F 7/40
See application file for complete search history.

(56) References Cited

U.S. PATENT DOCUMENTS

| 4,544,610 A | 10/1985 | Okamoto et al. |
| 7,006,859 B1 | 2/2006 | Amentani et al. |
| (Continued) | | |

FOREIGN PATENT DOCUMENTS

| CN | 102500055 | 6/2012 |
| EP | 1048319 | 11/2000 |
| (Continued) | | |

OTHER PUBLICATIONS

EPSEARCH, "14189810", Feb. 27, 2015, Feb. 27, 2015.

*Primary Examiner* — Richard Louis
(74) *Attorney, Agent, or Firm* — Haynes and Boone, LLP; J. Andrew Lowes

(57) ABSTRACT

A neural probe system having a single guide tube that is inserted into neural tissue and from which a number of neural probes can be deployed is described. Each probe is deployable into tissue along a desired trajectory. This is done by supporting the electrode array on a spring tape-type carrier that maintains axial stiffness once the neural probe has deployed out a channel in the guide tube. That way, a target neural tissue is bounded by an increased number of neural probes while minimizing trauma to surrounding body tissue.

20 Claims, 15 Drawing Sheets

(51) Int. Cl.
    *A61B 5/04*    (2006.01)
    *A61N 1/36*    (2006.01)
    *A61M 25/00*   (2006.01)
    *G03F 7/40*    (2006.01)
    *A61B 5/0478*  (2006.01)

(52) U.S. Cl.
    CPC ........ *A61M 25/003* (2013.01); *A61M 25/007* (2013.01); *A61N 1/0534* (2013.01); *A61N 1/36017* (2013.01); *G03F 7/40* (2013.01); *A61M 2025/0031* (2013.01)

(56) References Cited

U.S. PATENT DOCUMENTS

| | | | |
|---|---|---|---|
| 7,354,033 B1 | 4/2008 | Murphey et al. | |
| 7,551,951 B1 | 6/2009 | Osorio et al. | |
| 7,769,470 B1 | 8/2010 | Rezai et al. | |
| 7,941,202 B2 | 5/2011 | Hetke et al. | |
| 8,565,894 B2 | 10/2013 | Vetter et al. | |
| 2005/0075681 A1* | 4/2005 | Rezai .................. | A61N 1/0531 607/48 |
| 2007/0027514 A1 | 2/2007 | Gerber | |
| 2007/0106143 A1 | 5/2007 | Flaherty | |
| 2010/0191305 A1* | 7/2010 | Imran ................ | A61B 5/04004 607/45 |
| 2010/0292602 A1 | 11/2010 | Worrell et al. | |
| 2012/0303107 A1 | 11/2012 | Decré et al. | |
| 2012/0323288 A1 | 12/2012 | Anderson et al. | |
| 2013/0066182 A1 | 3/2013 | Seymour | |
| 2013/0090525 A1 | 4/2013 | Seymour et al. | |

FOREIGN PATENT DOCUMENTS

| | | |
|---|---|---|
| JP | 2007202727 | 8/2007 |
| KP | 1020120131815 | 5/2012 |

* cited by examiner

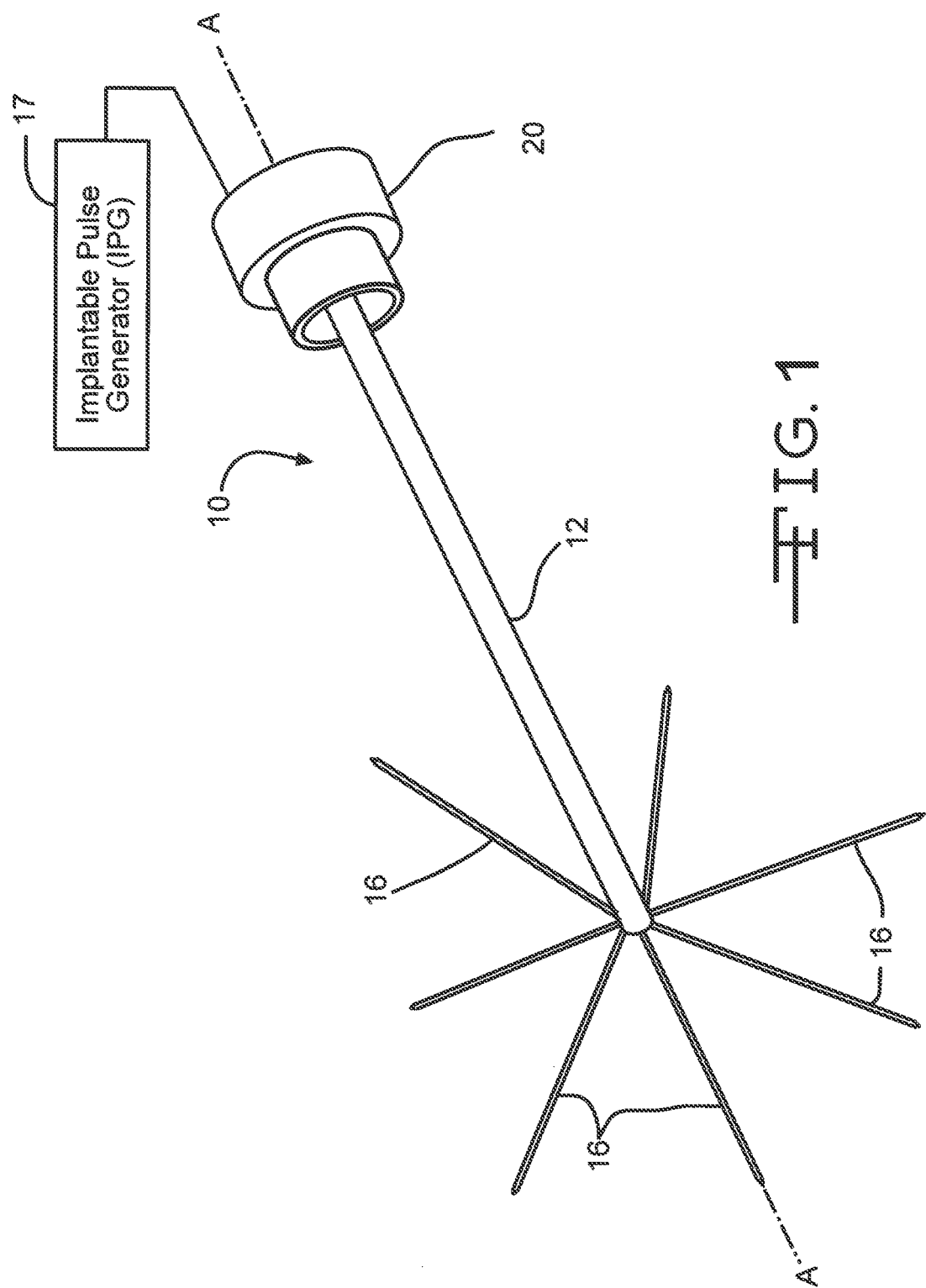

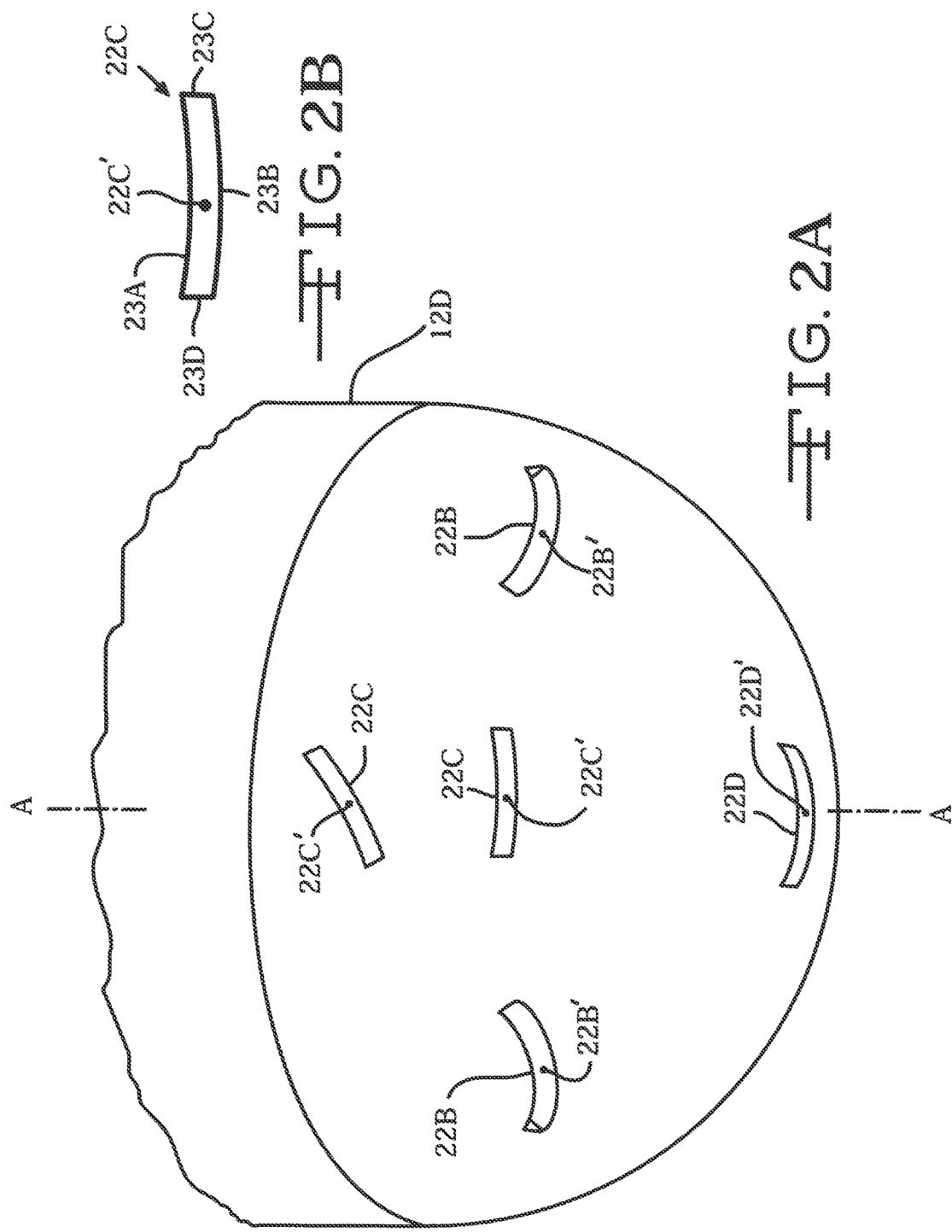

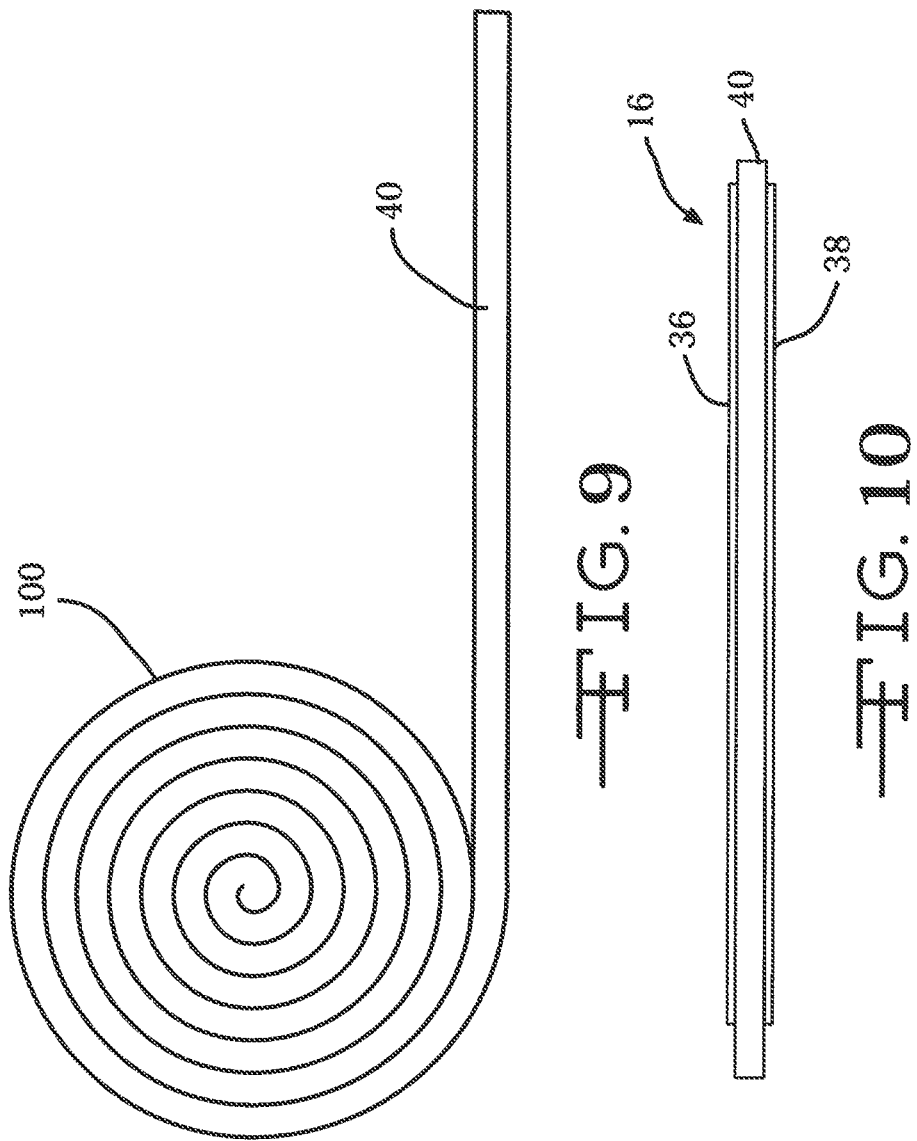

OMNIDIRECTIONAL DEPLOYABLE MULTICHANNEL NEURAL ELECTRODE SYSTEM

CROSS-REFERENCE TO RELATED APPLICATIONS

This application claims priority from U.S. Provisional Application Ser. Nos. 61/893,603, filed on Oct. 21, 2013 and 61/895,109, filed on Oct. 24, 2013.

BACKGROUND OF THE INVENTION

1. Field of the Invention

The invention relates to the field of devices and methods used for neural interventions. More particularly, the present invention relates to a neural probe comprising an electrode array of at least one of a stimulation electrode and a recording electrode. The electrode array is supported on a carrier having a shape and structure similar to a carpenter's tape spring. The tape spring-type carrier provides the electrode array with stiffness along a line of trajectory once deployed into body tissue, but with a degree of flexibility that allows the electrode array to move with the tissue.

2. Prior Art

Chronic Deep Brain Stimulation (DBS) devices (brain pacemakers) have emerged in the last decade as a revolutionary new approach to the treatment of neurological and psychiatric disorders. Conventional DBS therapy involves controllable electrical stimulation through a lead having four relatively large electrodes that are implanted in the targeted region of the brain. While conventional DBS therapy is generally safe and effective for reducing cardinal symptoms of the approved diseases, it often has significant behavioral and cognitive side effects and limits on performance. Additionally, the therapeutic effect is highly a function of electrode position with respect to the targeted volume of tissue, and more specifically, a function of which neuronal structures are influenced by the charge being delivered. With conventional electrodes, there are limitations as to how the charge is delivered and stimulation fields are limited as all of the electrode sites involved with stimulation are positioned along a single axis.

A neural lead or probe that is useful with DBS among a host of other interventional procedures is described in U.S. Pat. No. 8,565,894 to Vetter et al. The probe has a carrier of a rigid three-dimensional shape. An electrode array comprising stimulation and recording electrodes is supported on the rigid carrier. The distal end of a guiding element is connected to the proximal end of the carrier supporting the electrode array. While the carrier maintains its rigid three-dimensional shape, the guiding element is maneuverable from a first three-dimensional shape into a second, different three-dimensional shape. Since the carrier portion of the neural probe is rigid, as brain tissue and the like move, the electrode array is incapable of flexing and shifting to accommodate such movement.

Thus, there is a need for an improved neural intervention system for deployment of multiple neural probes to provide fine electrode positioning, selectivity, precise stimulation patterning, and precise lead location. However, the desire for such positional precision should not be so rigid as to be incapable of flexing and bending to accommodate tissue movement. The present invention provides such an improved and useful neural intervention system for placement of multiple neural probes in tissue, particularly brain tissue. That is done by supporting an electrode array on a tape spring-type carrier. The carrier provides an improved degree of stiffness along a line of trajectory once probe is deployed into body tissue, but allows for a degree of flexibility to accommodate movement of body tissue surrounding the neural probe.

SUMMARY OF THE INVENTION

Each thin-film neural probe electrode array according to the present invention is comprised of multiple metal traces and sites. As many as 100 conductive traces and electrode sites can be realized on an array that is as narrow as 30 microns and as thin as 6 microns. In order to be strong enough to be inserted into tissue, however, these neural probe electrode arrays must be either integrated during fabrication on a carrier that provides strength, or attached to a strengthening carrier post-fabrication. If the strengthening carrier is stiff, the electrode array can be inserted into tissue along a desired axial direction of a guiding element. In some cases, however, it is preferable to interface with tissue along a trajectory that is off-axis to the initial penetration of the guiding element. This requires a carrier that can deploy from the guiding element and follow a bend after penetration into body tissue and then maintain a straight trajectory after bending.

The use of tape spring-type carriers and the appropriate deployment device makes such insertion possible. Tape springs are used in a variety of deployable structures to serve as hinge mechanisms. An example is a carpenter's tape measure. It has geometric stiffness when extended, but can be guided around a corner. This is due to the curved cross-section of the structure. The normally curved cross-section results in a stiff U-beam structure that allows controllable one-directional axial motion (pulling the tape out or in). When the tape is pushed through a bend, the section of the tape in the bend flattens. As the tape is pushed past the bend, the spring returns to its curved U-beam state, again resulting in a stiff beam structure, but pointed axially in a new direction.

Accordingly, the present invention relates to a neural probe comprising an array of stimulation and/or recording electrodes supported on a tape spring-type carrier. The neural probe comprising the tape spring-type carrier is used to insert flexible electrode arrays straight into tissue, or to insert them off-axis from the initial penetration of a guide tube. Importantly, the neural probe is not rigid, but has a degree of stiffness provided by the tape spring-type carrier that maintains a desired trajectory into body tissue, but will subsequently allow the probe to flex and move in unison with movement of the body tissue. Additionally, an assembly is described to allow deployment of multiple thin-film neural probe electrode arrays from a single guide tube in a three-dimensional arrangement. Formation of the neural probe with the tape spring-type carrier, design of the electrode arrays, and the deployment mechanism are all described herein.

These and other objects will become apparent to one of ordinary skill in the art by reference to the following description and the appended drawings.

BRIEF DESCRIPTION OF THE DRAWINGS

FIG. 1 is a perspective view of a neural intervention system 10 according to the present invention.

FIG. 2A is an enlarged perspective view, broken away from FIG. 2, showing outlet ports 22C to 22E at the distal end of the guide tube 12.

FIG. 2B is an enlarged view of deployment port 22C shown in FIG. 2A.

FIG. 9 is a side elevational view of a roll 100 of tape spring material for one manufacturing method according to the present invention.

FIG. 10 is a side cross-sectional view of a neural probe 16 built by affixing a thin film electrode arrays 36 and 38 to opposed side of the tape spring from the roll 100 shown in FIG. 9.

DETAILED DESCRIPTION OF THE PREFERRED EMBODIMENTS

Figure 1A:
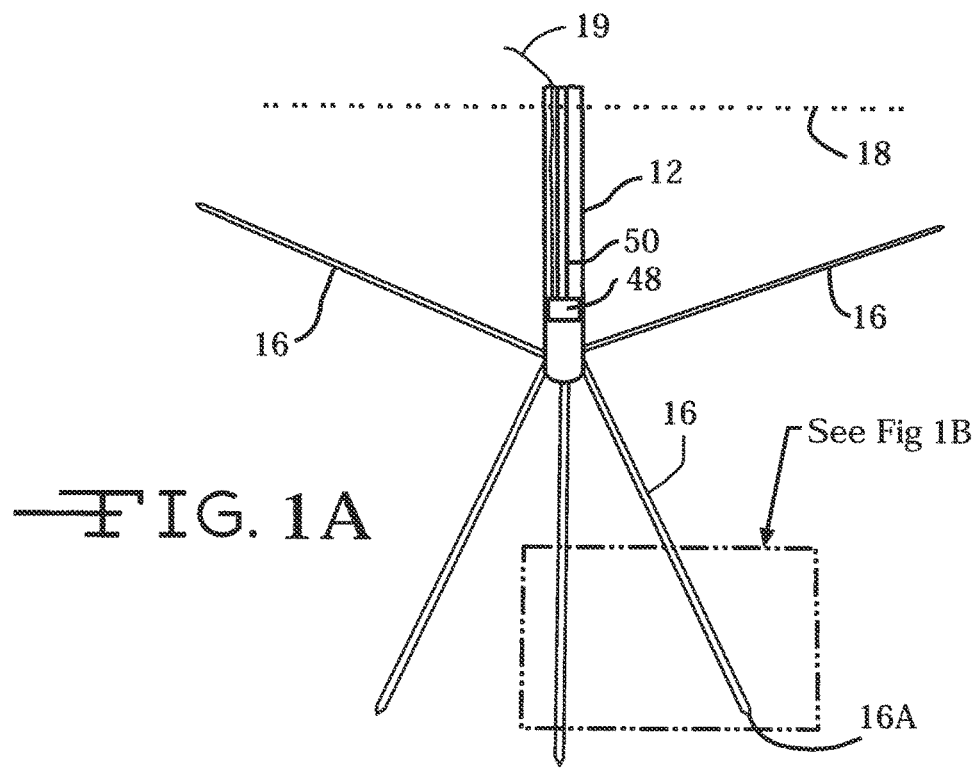
FIG. 1A is a schematic of the neural intervention system 10 residing in body tissue 18.

Turning now to the drawings, a general depiction of one embodiment of a neural intervention system 10 according to the present invention is illustrated in FIGS. 1 and 1A. The neural intervention system 10 comprises a guide tube 12 supporting a plurality of deployment channels 14 that are configured to direct the delivery of a number of neural probes 16 into body tissue 18. Among a host of possible interventional procedures, neural intervention system 10 is designed for use in deep brain stimulation procedures and more specifically, for interface with deep brain tissue in a three-dimensional manner. The neural intervention system 10 may alternatively be used in any suitable environment such as with the spinal cord, peripheral nerves, muscles, or any other suitable anatomical location.

The guide tube 12 is a conduit shaped structure having a side wall 12A extending along a longitudinal axis A-A from a distal portion 12B to a proximal end 12C connectable to a chamber 20. While shown having a cylindrical shape that is by way of example only. All that is required is that guide tube 12 has a sidewall defining a lumen. The chamber 20 is configured for attachment to a skull, preferably in a cranial burr-hole of a patient. Thin-film ribbon cables 19 run through the guide tube from the neural probes 16 to the chamber 20.

The chamber 20 is where the ribbon cables 19 connect to an electronic subsystem (not shown) that serves as an interface to any one of a number of external devices, such as implantable pulse generator (IPG) 17. Other electrical subsystems include, but are not limited to, a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable rechargeable battery, integrated electronics for either real-time signal processing of the input (recorded) or output (stimulation) signals, integrated electronics for control of the fluidic components, any other suitable electrical subsystem, or any combination thereof. Alternatively, the skull chamber 20 is not needed and the ribbon cables 19 connect directly to any one of the above listed external devices.

Figure 3A:
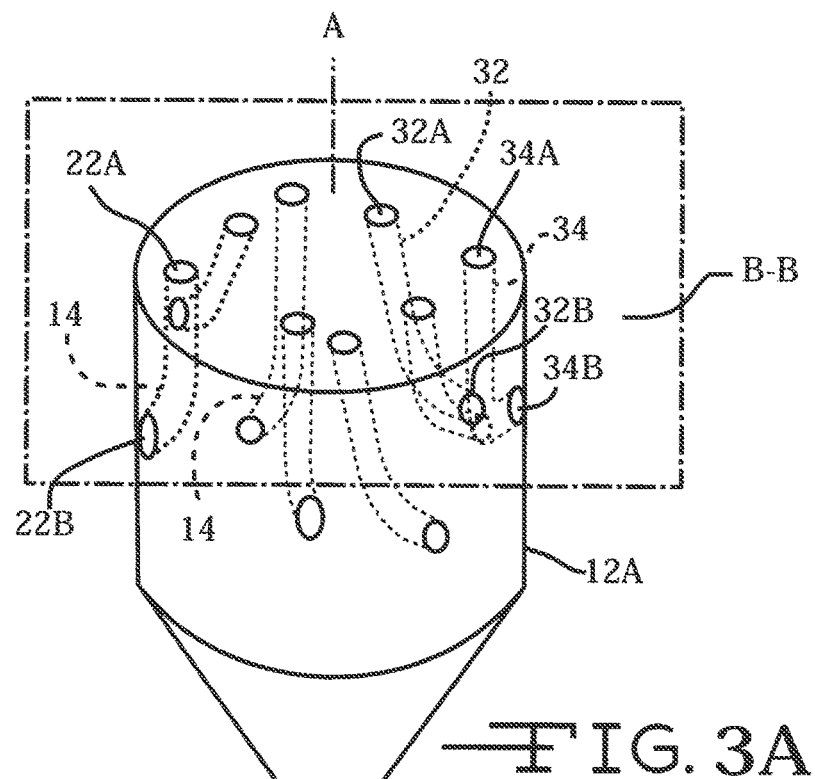
FIG. 3A is a perspective view of the distal portion of the guide tube 12 including the deployment channels 14 shown in FIG. 2.

The guide tube 12 is preferably made of a rigid material that can be inserted into tissue or other substances without buckling and can maintain a generally straight trajectory through the tissue 18. The material may be uniformly rigid, or rigid only in a particular direction (such as the axial direction). The guide tube material is preferably plastic (such as a medical grade plastic) or metallic (such as titanium), but may alternatively be any suitable material such as metal or a combination of materials. The distal tube portion 12B includes a rounded or curved tip 12D designed to prevent undue trauma to body tissue as the guide tube is inserted therein. FIG. 3A illustrates an alternate embodiment of a sharpened tip 12D' adapted to penetrate tissue and aid in insertion of the guide tube therein.

It is within the scope of the present invention that the guide tube 12 is maneuverable into the tissue in a three-dimensional arrangement. Such a maneuverable guide tube 12 may include a system of cables, joints, connections, or robotics that is controlled by a user to position the guide tube in a desired position in the tissue. The maneuverable guide tube 12 may also be guidable remotely and/or wirelessly.

Figure 4:
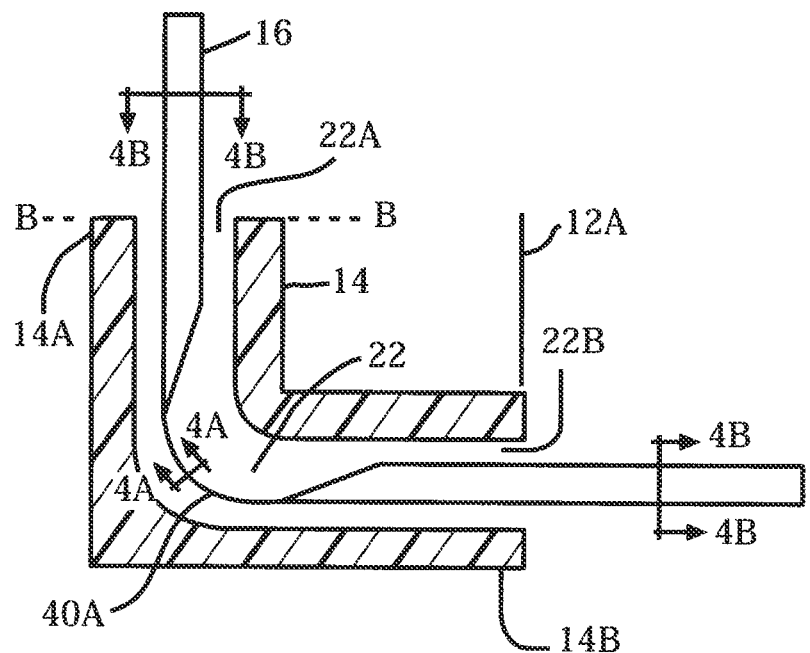
FIG. 4 is a schematic of an exemplary deployment channel 14.

The distal portion 12B of the guide tube includes at least one, and preferably a plurality of deployment channels. Exemplary deployment channel 14 (FIG. 4) comprises a proximal channel portion 14A spaced from a distal channel portion 14B. The exemplary deployment channel 14 has a lumen 22 extending from a proximal open end 22A adjacent to the proximal channel portion 14A to a distal open end 22B adjacent to the distal channel portion 14B. As will be described in greater detail hereinafter, the proximal and distal open ends 22A, 22B are not aligned along a common axis. Instead, lumen 22 extends from a proximal open end 22A residing along a plane B-B aligned substantially perpendicular to the longitudinal axis A-A of the guide tube 12 to a distal open end 22B serving as an open port at the guide tube sidewall 12A. Although by way of example only, the path from the proximal open end 22A to the distal open end 22B is substantially a right angle.

Figure 3B:
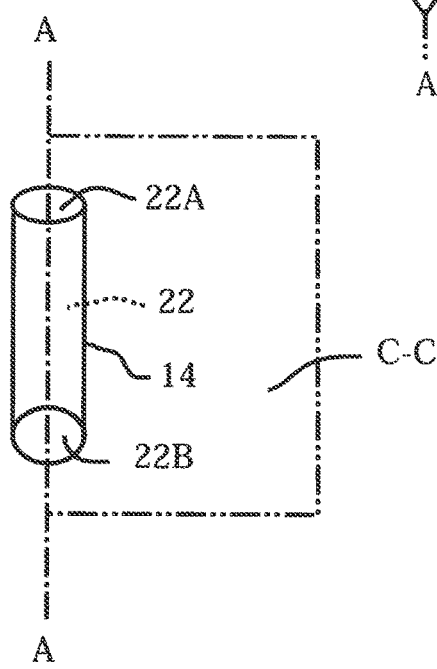
FIGS. 3B and 3C are schematic views of deployment tubes 14 and 24 showing exemplary paths of their open conduits 22 and 24 with respect to planes C-C and D-D aligned with longitudinal axis A-A.
Figure 3C:
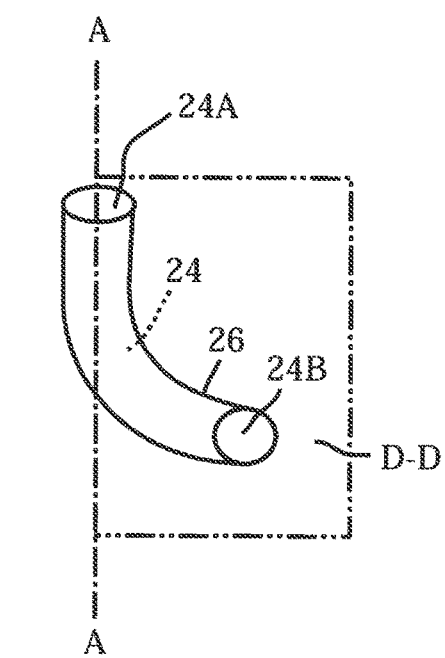

FIG. 3B illustrates an embodiment where the lumen 22 from proximal open end 22A to distal open end 22B of channel 14 is bisected by an imaginary plane C-C aligned along axis A-A. FIG. 3C illustrates the lumen path 24 of a second exemplary one of the deployment channels 26 deviating from a proximal open end 26A bisected by plane D-D aligned along axis A-A to a distal open end 26B angularly deviating from plane D-D. As seen from the perspective of a plan view looking down on the proximal end 12C of guide tube 12 and along axis A-A, the angular deviation can be in either the clockwise or counter-clockwise directions.

A third exemplary one of the deployment channels 32 has its proximal open end 32A residing along the imaginary plane B-B aligned perpendicular to axis A-A and with its distal open end 32B exiting the guide tube sidewall 12A so that the lumen follows a path forming a substantially obtuse angle with respect to axis A-A. A fourth exemplary one of the deployment channels 34 has its proximal open end 34A residing along the imaginary plane B-B, but with its distal open end 34B exiting the guide tube sidewall 12A so that the lumen follows a path forming a substantially acute angle with respect to axis A-A. Those skilled in the art will readily understand that a deployment channel can provide a lumen that follows a path incorporating a combination of those described with respect to the first to the fourth exemplary channels 14, 26, 32 and 34. According to the present invention, the trajectory of the distal channel portion defining the distal open end 22B, 32B and 34B ranges from about 10° to 180° with respect to axis A-A. Moreover, it is noted that distal open end 32B is more proximal than distal open end 34B. That is even though their respective proximal open ends 32A, 34A reside along plane B-B.

Thus, the exemplary deployment channels 14, 26, 32 and 34 can be angled in many different orientations. That is for the purpose of introducing a plurality of neural probes 16 into a target body tissue at any one of a number of trajectories off axis from axis A-A of the guide tube 12. This greatly improves the footprint of deployed electrodes so that multiple spatially separate stimulation and recording channels radiate outwardly from the distal portion 12B of the guide tube. Enhanced deployment of neural probes 16 makes it possible to spontaneously record neuronal activity, movement-related activity, or evoked activity as a result of stimulation from nearby sites. Simultaneously sampled recordings could be exploited to increase the speed and accuracy by which data are acquired. With respect to stimulation, this three-dimensional arrangement of neural probes 16 can be used in either monopolar or bipolar modes to steer current to desired body tissue locations.

Figure 2:
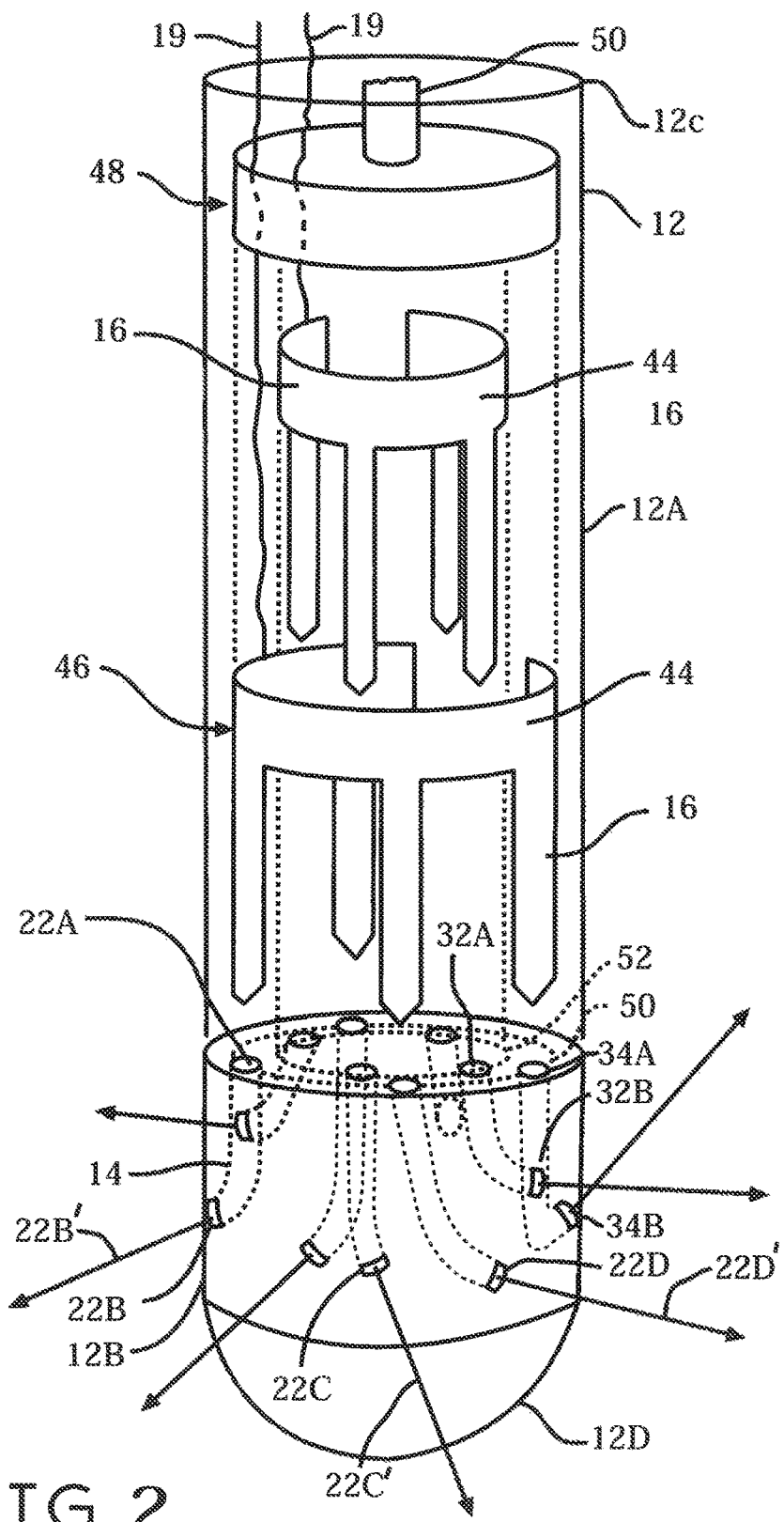
FIG. 2 is a schematic of the neural intervention system 10 shown in FIG. 1 including deployment channels 14 and neural leads 16.

FIG. 2A is an enlarged view of the distal end 12D of the guide tube. This view shows that the distal open ends 22B of exemplary deployment channel 14 can reside on the distal guide tube end 12D. That is in addition to or instead of the distal open end of a channel residing on the cylindrical sidewall 12A as shown in FIG. 2. While it is preferred that the distal open end of a deployment channel have an elongate shape with opposed curved sidewalls, that is not necessary. Open end 22C has a rectangular shape without curved sidewalls. There is also an open end 22D for a deployment channel aligned along the longitudinal axis A-A.

Figure 4A:
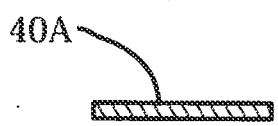
FIG. 4A is a cross-sectional view taken along line 4A-4A of FIG. 4.

FIGS. 4, 4A, 4B, 5, 5A and 5B illustrate a novel aspect of a neural probe 16 according to the present invention. The neural probe 16 comprises opposed first and second electrodes 36 and 38 comprising an electrode array supported by a tape-spring-type carrier 40. The carrier 40 is of a metal, preferably selected from tungsten, stainless steel, platinum-iridium, or of a polymeric material, and in an unstressed condition has a shape similar to a carpenter's tape for a tape measure. The tape spring-type carrier 40 flexes to permit the neural probe 16 to readily bend, thereby when in a stressed condition collapsing into a shape having a linear cross-section 40A (FIG. 4A) perpendicular to the length of the carrier as the probe moves along a bend in the lumen 22 of exemplary deployment channel 14. That portion of the tape spring-type carrier 40 residing in the proximal portion 14A of the deployment channel 14 adjacent to the proximal open end 22A has the concave tape spring-type shape 40B (FIG. 4AB). Similarly, that portion of the carrier 40 residing in the distal portion 14B of the deployment channel adjacent to the distal open end 22B and extending out therefrom has re-assumed the tape spring shape. The tape spring-type shape of the carrier 40 provides the neural probe 16 with a degree of linear rigidity along the trajectory of the distal channel portion 14B and outwardly therefrom that is not available with prior art probes.

Figure 4B:
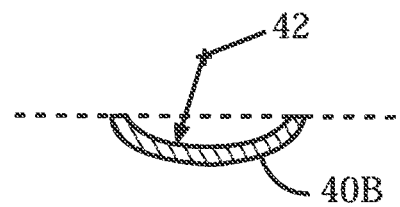
FIG. 4B is a cross-sectional view taken along line 4B-4B of FIG. 4.

FIG. 4B shows that the curved cross-sectional shape of the tape spring-type carrier 40 can be concave having a focal point 42 residing outside plane E-E extending through the carrier's opposed ends. The curve cross-sectional shape of the tape spring-type carrier can also be that of a parabola.

Figure 5:
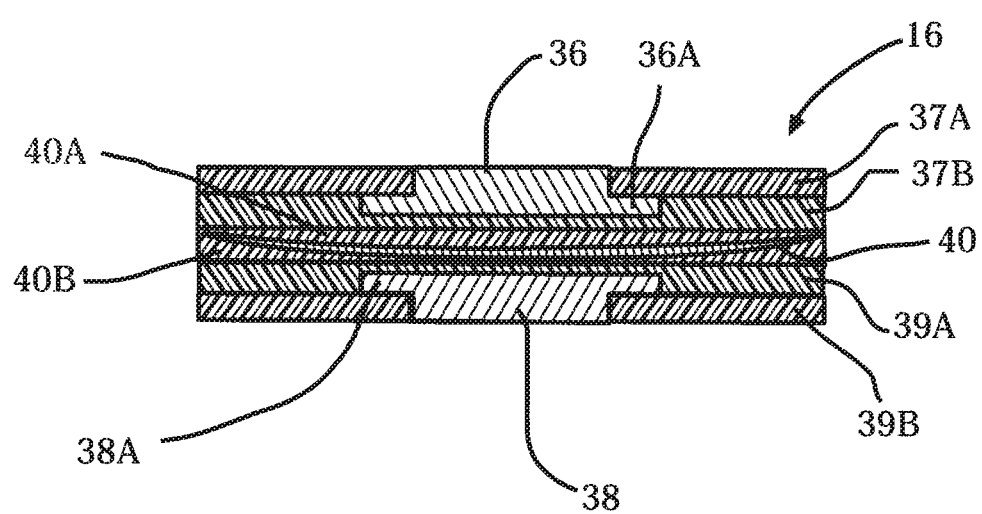
FIG. 5 is a cross-sectional view of neural probe 16 showing planar electrodes 36 and 38 supported on opposite sides of a tape spring-type carrier 40 according to the present invention.
Figure 5A:
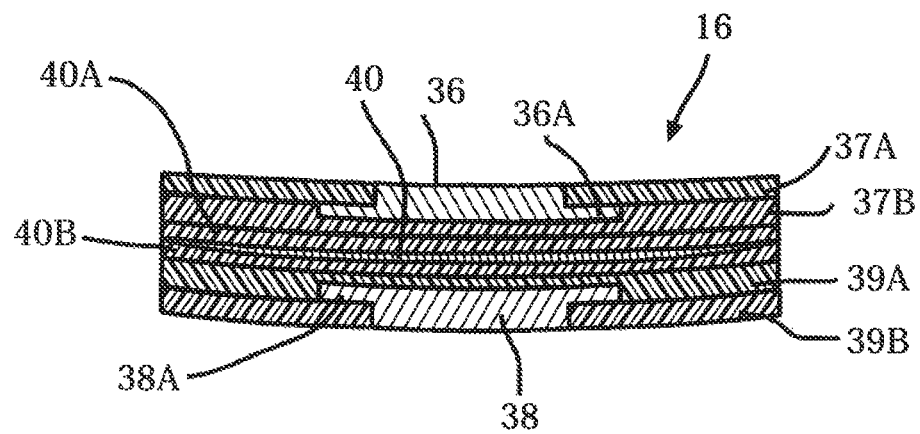
FIG. 5A is a cross-sectional view of a neural probe 16 similar to that shown in FIG. 5, but with electrodes 36 and 38 having a curved shape.
Figure 5B:
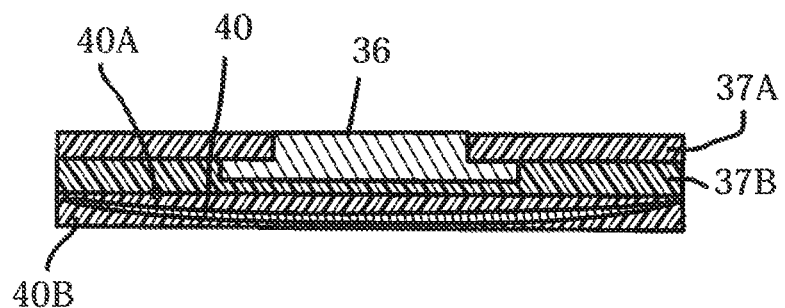
FIG. 5B is a cross-sectional view of the neural probe 16 shown in FIG. 5A, but with only one electrode 36 supported on the tape spring-type carrier 40.

FIGS. 5, 5A and 5B show the tape spring-type carrier 40 sandwiched between opposed polymeric layers 40A and 40B. If the carrier 40 is of a polymeric material, then layers 40A and 40 are of a different polymeric material. Electrode 36 is exemplary of a stimulation electrode while electrode 38 is exemplary of a recoding electrode. The stimulation electrode 36 is configured for electrical stimulation of biological tissue and recording electrode 38 is configured for recording of biological activity from biological tissue. The stimulation electrode 36 is sandwiched between opposed dielectric layers 37A and 378. Likewise, recording electrode 38 is sandwiched between opposed dielectric layers 39A and 39B. The electrode sites 36, 38 are preferably metal such as iridium, platinum, gold, but may alternatively be any other suitable material. Polyimide, parylene, inorganic dielectrics such as silicon carbide or aluminum oxide, or a composite stack of silicon dioxide and silicon nitride is preferably used for the dielectric layers 39A, 39B.

The enlarged portions 36A and 38A depict electrical interconnects running the length of the neural probe. In an alternate embodiment (not shown) interconnects 36A, 38A are of a lesser cross-section than the respective electrodes 36, 38. The conductive interconnects 36A, 38A are preferably metal or polysilicon, but may alternatively be any other suitable material. Interconnects 36A and 38A preferably terminate with electrical contacts or bond pads (not shown) at their proximal ends. That is for electrical connection of the electrodes 36, 38 to external instrumentation and/or hybrid chips, such as depicted by IPG 17 in FIG. 1. For more detail regarding suitable configurations for electrodes and interconnects for use with neural probes 16, reference is made to U.S. Pat. No. 7,941,202 to Hetke et al., which is assigned to the assignee of the present invention and incorporated herein by reference.

FIG. 5A shows the entire electrode structure having a curved shape mimicking that of the tape spring-type carrier. This is contrast to the electrode structure shown in FIG. 5 having generally planar electrode faces. FIG. 5B shows an electrode supported on only one side of the tape spring-type carrier 40.

Figure 1B:
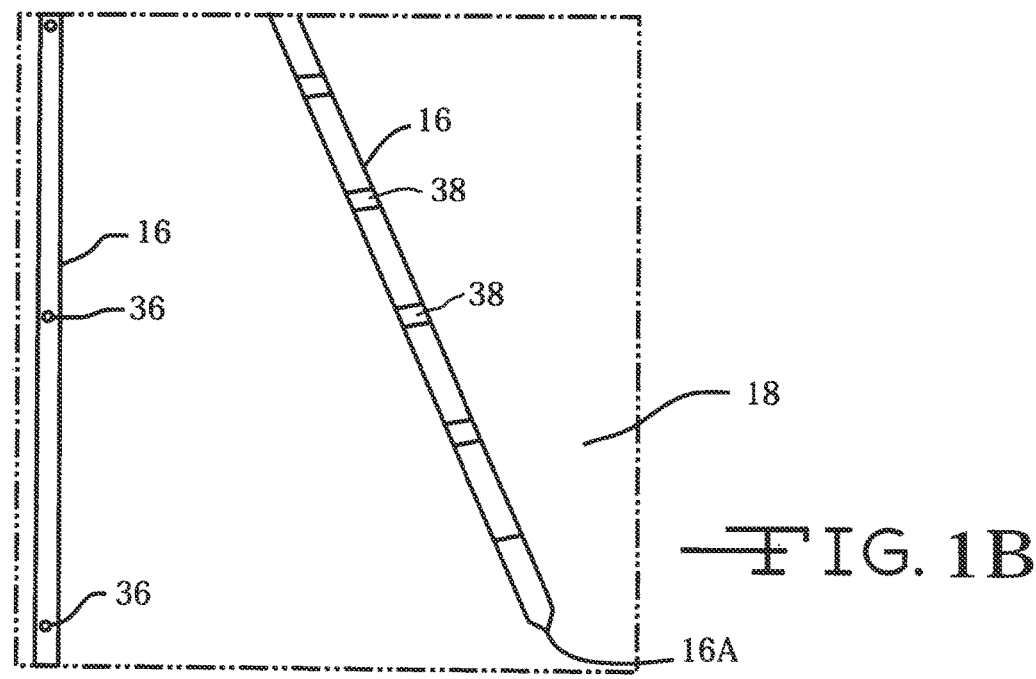
FIG. 1B is an enlarged view of the designated area from FIG. 1A.

In one exemplary embodiment of the neural probe 16 shown in FIGS. 1, 1A and 1B, the electrode array preferably includes sixty-four stimulation electrodes 36 and thirty-two recording electrodes 38 positioned around and along the tape spring-type carrier 40. Each stimulation electrode site 36 has a surface area of preferably 0.196 mm$^2$ (diameter=500 µm), but may alternatively have any suitable surface area or shape. Each recording electrode site 38 has a surface area of preferably 0.00196 mm$^2$ (diameter=50 µm), but may alternatively have any suitable surface area or shape. Stimulation sites are also preferably spaced at 750 µm in the axial direction (center-to-center) and positioned at sixteen successive locations. Between each row of stimulation electrode sites 36, two recording electrode sites 38 are preferably positioned on opposite sides of the tape spring-type carrier 40. The position of each recording electrode site pair 38 preferably shifts ninety degrees between successive depths. Alternatively, there may be any suitable number of stimulation sites 36 and recording electrode sites 38, and the stimulation electrode sites and recording sites may alternatively be positioned in any other suitable arrangement.

Referring back to FIG. 2A, the enlarged views of deployment opening 22C, 22D and 22E are designed with central axes aligned along a desired trajectory line. The trajectory lines come out of the page and are depicted by the respective points 22C', 22D' and 22E'. The respective axes are centered between the opposed major and minor sidewalls of the opening. FIG. 2B is an enlarged view of representative deployment opening 22C showing opposed major sidewalls 23A and 23B and opposed minor sidewalls 23C and 23D. Axis 22C' is centered therein and represents the trajectory a neural probe 16 comprising the tape spring-type carrier 40 of the present invention would take after having been deployed out from the opening 22C. Representative trajectories 22B', 22C' and 22D' are also shown in FIG. 2.

Figure 7:
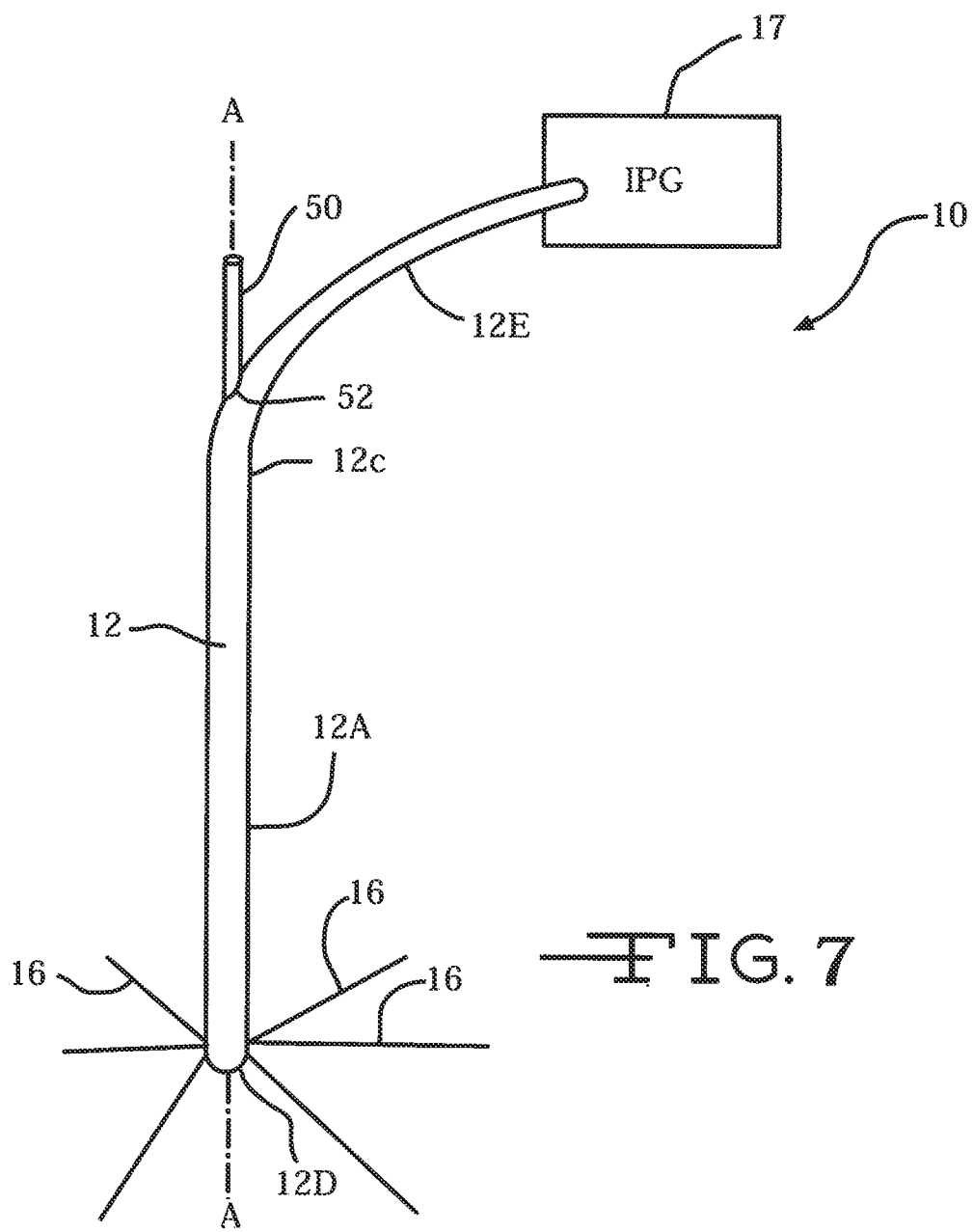
FIG. 7 is a perspective view of an alternate embodiment of a neural intervention system 10B according to the present invention connected to an IPG 17.

With further reference to FIG. 2, the neural probes 16 are connected to a manifold 44. Thin-film ribbon cables 19, which connect from the manifolds 44 to an electronic subsystem (not shown), serve as an interface to any one of a number of external devices, such as implantable pulse generator (IPG) 17 (FIGS. 1 and 7). The probes 16 comprising the tape spring-type carrier 40 extend distally from the manifold 44 and are spaced at even or uneven intervals from each other. Moreover, the guide tube 12 can support more than one manifold/neural probe assembly. Two such assemblies 46, 48 are illustrated, but that is by way of example. In any event, the neural intervention system 10 is constructed with the probes pre-registered with their respective channels. As previously discussed, FIG. 3A, which is similar to FIG. 2, illustrates that the proximal open ends of the plurality of deployment channels are located along common plane B-B, substantially perpendicular to axis A-A. The respective proximal open channel ends are arranged in concentric circles, the outer circle 50 corresponding to the first manifold/neural probe assembly 44 and the inner circle 52 corresponding to the second manifold/neural probe assembly 46. The respective distal ends of the probes 16 are received in the proximal open ends of the channels 14.

FIG. 2 further shows an actuation mechanism for deploying the plurality of neural probes 16. The actuation mechanism includes a plunger 48 connected to the first and second manifold/neural probe assembly 44, 48. The distal face of plunger 48 has grooves (not shown) that are sized and configured to receive the upper edges of the respective manifolds 44 therein. The opposite face of the plunger 48 supports a push rod 50. The push rod extends to the proximal end 12C of the guide tube and has a length that is sufficient for a user to grasp and manipulate to move the plurality of probes 16 through their respective deployment channels and out the open ends thereof. The neural probes 16 are of a sufficient length that with the plunger 48 moved distally along the tube 12 until the manifolds 44 are adjacent to the proximal open ends of the deployment channels, the probes extend through the exemplary deployment channels 14, 26, 32 and 34 and out the distal open ends thereof to penetrate tissue at distances sufficient to provide effective stimulation or recording capability. While two manifold/neural probe assemblies are shown in FIG. 2, it is within the scope of the present invention that three or more such assemblies can be fitted into a single guide tube 12.

FIGS. 1A and 1B illustrate the guide tube 12 inserted into tissue 18 with a plurality of neural probes 16 deployed in a three-dimensional arrangement into the tissue. The tape spring-type carrier 40 of the present invention shuttles the neural probes 16 into tissue or other substances in a straight-line or radial direction once the probe has exited the distal open end of its deployment channel. Moreover, the carrier 40 may include a sharpened end 16A adapted to penetrate tissue and aid in insertion of the neural probe 16 including the carrier 40 into tissue at trajectories off axis from that of the penetrating guide tube 12. Importantly, the carrier 40 is not a rigid structure. Instead, the carrier has sufficient stiffness to follow a desired trajectory dictated by the trajectory axis of one of previously described exemplary opens 22C, 22D and 22E, but that will move in response to movement of the tissue into which the probe 16 has been deployed. That helps to prevent undue trauma to the body tissue while maintaining a desired degree of stimulation and recording efficacy.

Figure 6:
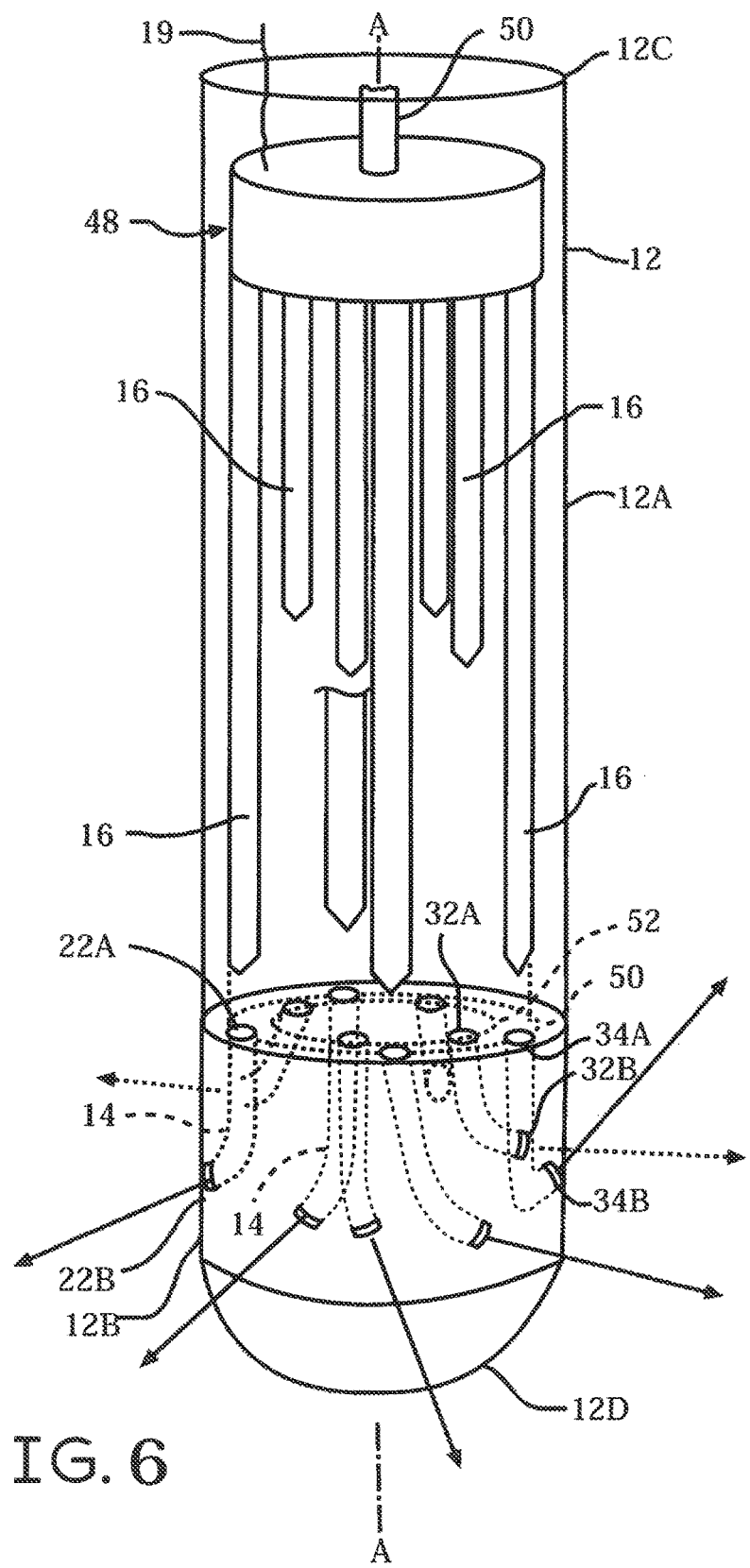
FIG. 6 is a perspective view of a neural intervention system 10A similar to that shown in FIG. 2 but with the plurality of neural probes 16 directly connected to a plunger 48 and push rod 50 as an actuation mechanism.

FIG. 6 illustrates another embodiment of a neural intervention system 10A according to the present invention. System 10A is similar to that shown in FIG. 2 except that the actuation mechanism for deploying the plurality of neural probes 16 does not include a manifold. Instead, the neural probes 16 are individually directly connected to the plunger 48 connected to the push rod 50. A thin-film ribbon cable 19, which connects from the manifolds 48 to an electronic subsystem (not shown), serves as an interface to any one of a number of external devices, such as implantable pulse generator (IPG) 17 (FIGS. 1 and 7).

FIG. 7 illustrates another embodiment of a neural intervention system 10B according to the present invention. System 10B is similar to the system 10 shown in FIG. 1 except that the guide tube 12 has a branched portion 12E extending from the proximal guide tube end 12C. The branched tube portion 12E houses the ribbon cables (not shown, but similar to those designated as 19 in FIG. 1A) connected to IPG 17 as an exemplary electronic subsystem. There is also an open port 52 where the proximal guide tube portion 12C meets the branched tube portion 12E. Port 52 provides an exit for push rod 50 of the actuation mechanism for deploying the plurality of neural probes 16 into tissue 18.

Figure 8:
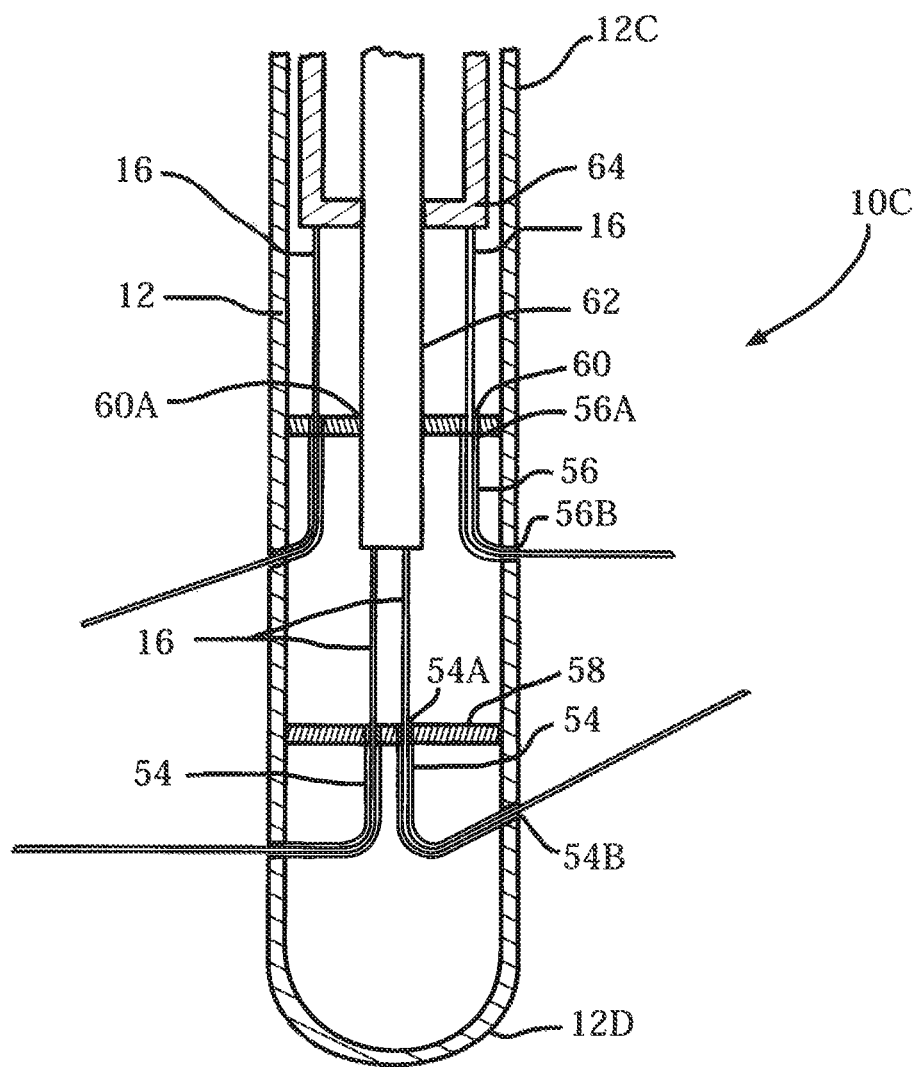
FIG. 8 is a side cross-sectional view of a neural intervention system 10C according to the present invention with deployment channels 54 and 56 at different elevational levels along the guide tube 12 and with respective push rods 62 and 64 for deploying neural probes therefrom.

FIG. 8 illustrates a further embodiment of a neural intervention system 10C. This embodiment shows that it is within the scope of the present invention that guide tube 12 can support a first, and preferably a plurality of first deployment channels 54 at a more distal location than a second, and preferably a plurality of second deployment channels 56.

The first deployment channels 54 have their proximal ends 54A supported by plate 58 connected to an inner surface of the guide tube sidewall 12A. The distal open ends 54B provide a port in the guide tube sidewall 12A adjacent to the distal tube portion 12D. The proximal ends 56A of the second deployment channels 56 are likewise supported by a second plate 60 connected to the inner guide tube sidewall. Their distal open ends 56B provide a port in the guide tube sidewall 12A adjacent to the proximal tube end 12C.

A first push rod 62 serving as an actuation mechanism extends through an opening 60A in the second plate 60 and is connected to the proximal ends of neural probes 16 in registry with the first deployment channels 54. A second push rod 64 serves as an actuation mechanism for deploying neural probes 16 in registry with the second deployment channels 56. It is noted that the proximal ends of first deployment channels 54 are radially closer to the longitudinal axis A-A than the proximal ends of the second deployment channels 56. That is to provide clearance so that the first push rod 62 does not interfere with the second push rod 64.

It will be understood by those skilled in the art that the structure of push rods 62 and 64 is for the purpose of illustration only. Other structural configurations are within the scope of the present invention. Moreover, while first and second sets of deployment channels 54, 56 are shown, it is within the scope of the present invention that there can be two, three or more deployment channels delineated from each other not by where their respective distal open ends exit the guide tube sidewall 12A, but where their proximal open ends reside inside the guide tube with respect to each other.

FIGS. 9 and 10 illustrate one method of making a neural probe according to the present invention. A metal or composite tape spring 40 is provided in a roll. The tape spring material is rolled out and fabricated to a desired shape. The electrode structures 36 and 38 shown in FIGS. 5, 5A and 5B are then affixed, such as with a suitable medical grade adhesive, to one or both sided of the tape spring-type carrier 40.

FIGS. 11 to 17 illustrate the steps for forming a neural probe 16 incorporating a tape spring-type carrier 40 according to a second embodiment of the present invention.

Figure 11:
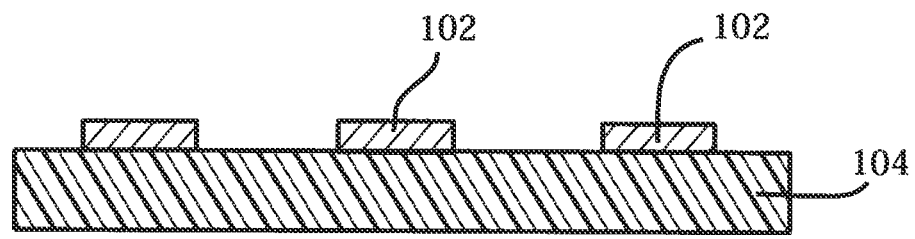
FIGS. 11 to 17 illustrate another embodiment of a photoresist process for manufacturing the tape spring-type carrier 40 of a neural probe 16 according to the present invention.

FIG. 11 shows a photo-resist material 102 is deposited on a manufacturing substrate 104. The photo-resist 102 is patterned in a shape similar to that desired for the product tape spring-type carrier 40. The substrate 104 is preferably made of glass or silicon, but may alternatively be made from any other suitable material. The substrate 104 may be flexible, rigid, or semi rigid depending on the microfabrication tooling (organic electronics equipment can increasingly use flexible substrates such as in roll-to-roll manufacturing, whereas IC and MEMS microfabrication equipment use a rigid silicon substrate). The substrate 104 has a thickness ranging from about 200 microns to about 925 microns, preferably greater than 500 microns.

The photo-resist material 102 is preferably a thin film of gel, photoresist, or other transparent or semi-transparent organic medium that can be patterned onto the substrate 104. The photo-resist film 102 is preferably at least semi-transparent to allow passage of light from a UV light source through the photoresist material. For positive photoresists, the area that is exposed to the UV light can be developed away in a developer. For negative photoresist, polymer at the area that is exposed to the UV light forms strong chemical bonds that can withstand a developer, while the unexposed area can be developed away in a developer. The photo-resist film 102 can be deposited, patterned, exposed to UV light, and developed in any suitable thin film technique.

Figure 12:
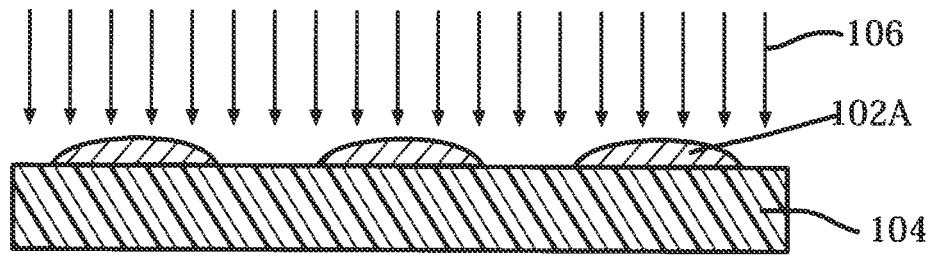

FIG. 12 illustrates that the photoresist 102 is subjected to heat so that it flows and forms a curved or parabolic upper surface 102A to the substrate 104 of a shape approximating the final tape spring-type carrier shape. Then, the heated photoresist is subjected to a Deep Reactive Ion Etching (DRIE) 106 process to duplicate the photoresist pattern 102A on the substrate upper surface 104A. After the DRIE process, the resulting structure will be cleaned by oxygen plasma or standard organic and inorganic wet cleaning process.

Figure 13:
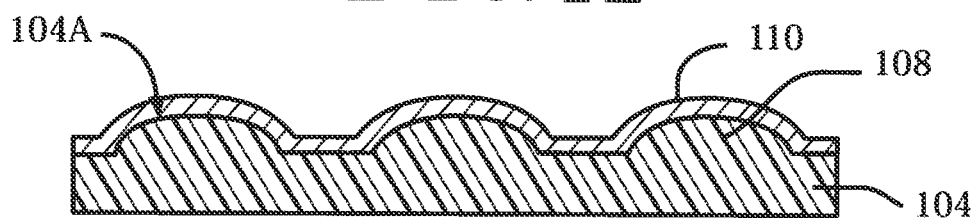
Figure 14:
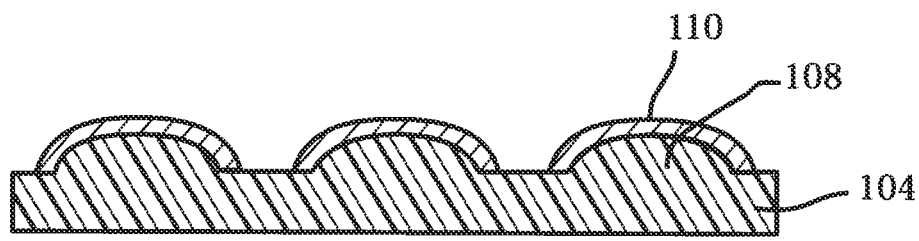

FIG. 13 shows that after cleaning, a metal or polymeric carrier layer 110 is deposited on the upper or outer surface 104A of the substrate. The carrier layer 110 can be deposited using any suitable thin film, semiconductor, microelectromechanical systems (MEMS) manufacturing technique or other microfabrication process, such as physical vapor deposition. Exemplary techniques and processes include evaporation and sputtering deposition. The carrier layer 110 preferably includes thermal conductive or electrical conductive material such as of platinum (Pt) or platinum-iridium, iridium oxide, titanium nitride, or any other metal, metal oxide, shape memory alloy, or conductive polymer having suitable electrically conductive properties. The carrier layer 110 can also be of a polymeric material, such as of polyimide, but may alternatively be made from any other suitable material. Moreover, the carrier layer 110 can be of a resorbable material, which is resorbed into tissue after a period of time. With the carrier supporting an electrode array, upon resorption, the electrode array is left to float freely in the brain or other suitable tissue or material. The bioresorbable polymer is preferably polyglycolide or polylactide, but may alternatively be made from any suitable bioresorbable material.

The carrier layer 110 is shown as a continuous layer and can be patterned (FIG. 14) using any suitable wet etch or dry etch technique. The mask (not shown) is a photodefined resist or any other masking material patterned directly or indirectly using standard photolithography techniques. After the carrier layer 110 is patterned, excess metal or polymeric layer is etched away, leaving the pattern of the tape spring behind. A lift-off process, as is well known to those skilled in the art, can also be used to leave the tape spring pattern.

Figure 15:
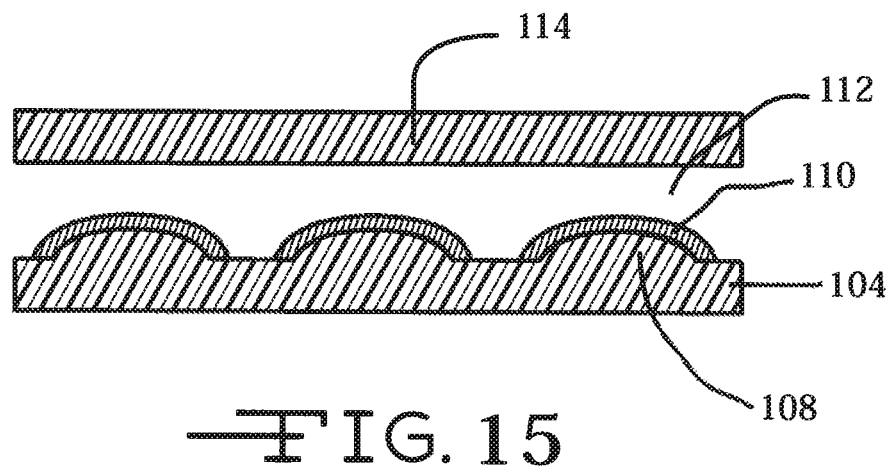

FIG. 15 illustrates that polydimethylsilisane (PDMS) as an exemplary transfer material 112 is spun onto the carrier patterns 110 followed by mounting a second manufacturing substrate 114 thereon. Polyimide can be used at this step instead of PDMS. In this case, electrodes can be fabricated on the polyimide film before undergoing the layer transfer onto a new carrier.

The original manufacturing substrate 104/108 is removed exposing curved inner surfaces 110A of the patterned tape spring-shaped material. This can be achieved by wet or dry etching technique.

Figure 16:
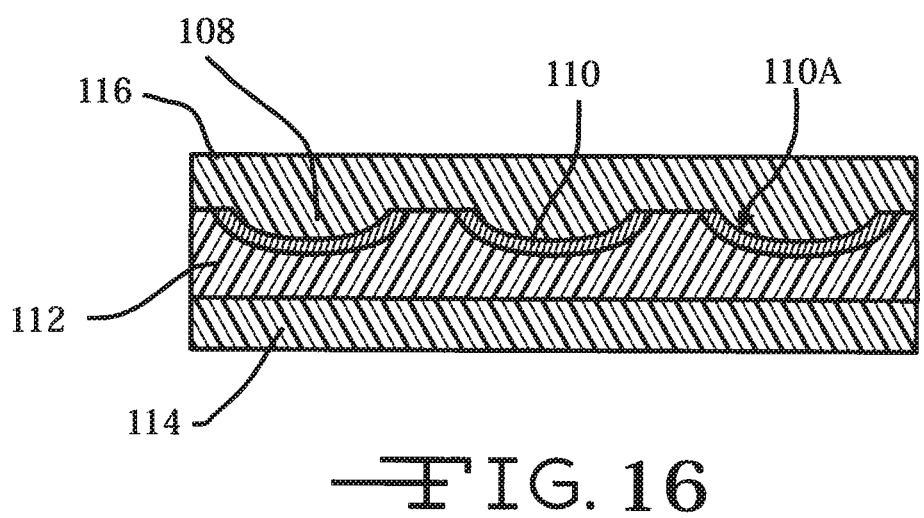

FIG. 16 shows that the second manufacturing substrate 114 is flipped upside down, and a polyimide material 116 is spun coated onto the exposed curved inner surfaces 110A.

Figure 17:
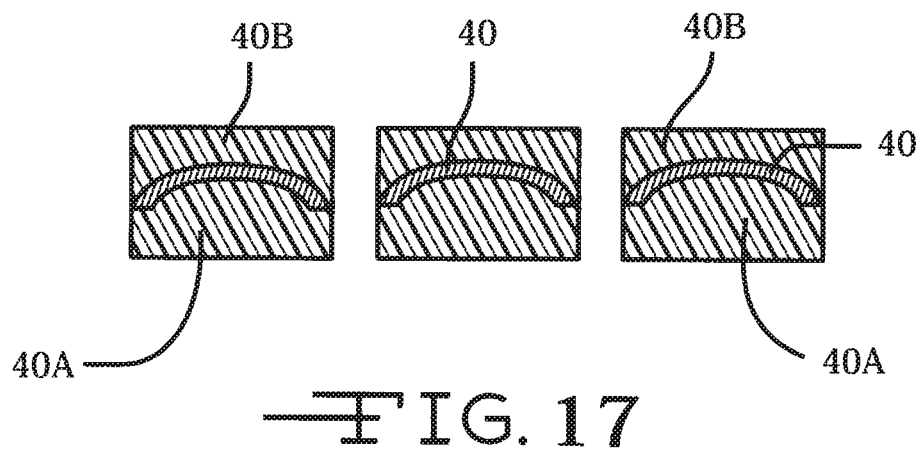

FIG. 17 illustrates that a photolithography process is used to define the shape of the thusly fabricated tape spring-type carrier 40 with polyimide layers 40A and 40B coated on both sides. The result is the tape spring-type carrier 40 sandwiched between polymeric layers 40A, 40B shown in FIGS. 5, 5A and 5B.

Figure 18:
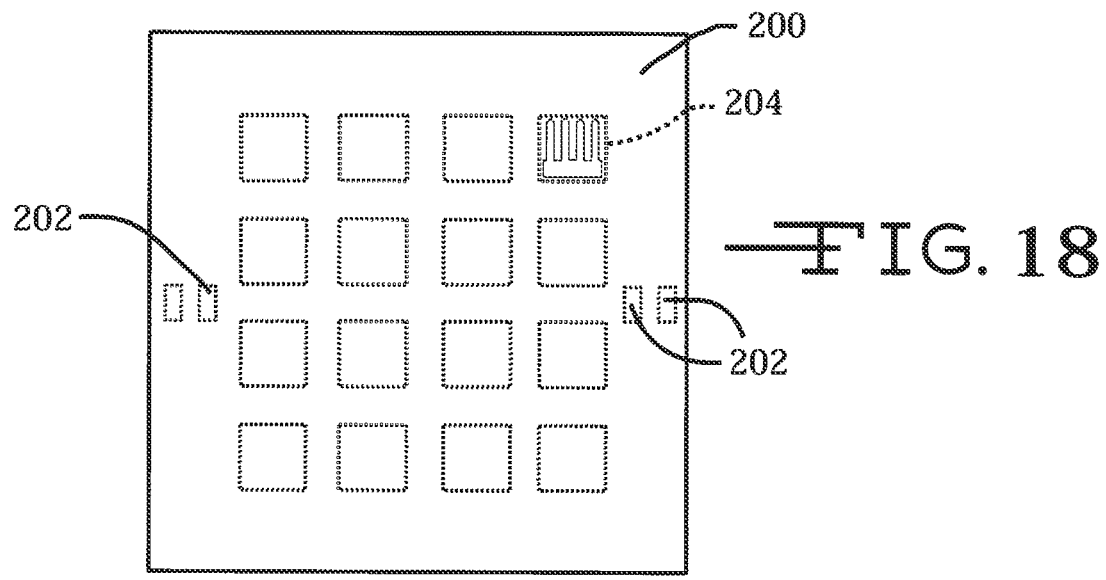
FIGS. 18, 18A and 18B illustrate another embodiment of a process of microstamping, nanoimprinting or fluting of sheet metal for manufacturing the tape spring-type carrier 40 of a neural probe 16 according to the present invention.
Figure 18A:
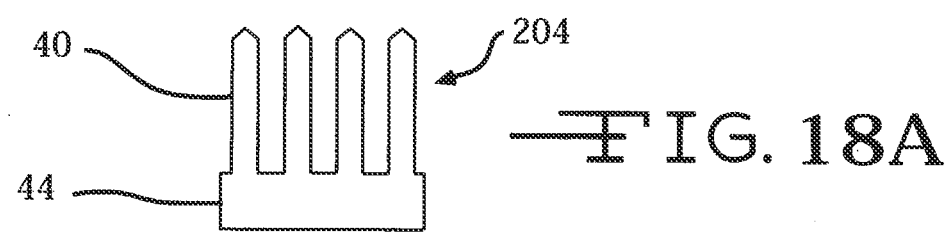
Figure 18B:
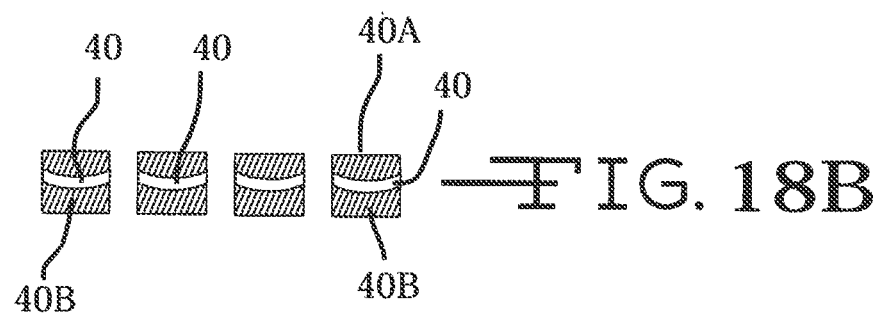

FIGS. 18, 18A and 18B illustrate the steps for forming a neural probe 16 incorporating a tape spring-type carrier 40 according to a third embodiment of the present invention.

FIG. 18 shows a sheet of metal 200 including patterned carrier 40 and registration patterns 202. The registration patterns 202 provide for registering the carrier sheet 200 to the electrode manufacturing substrate as shown in FIGS. 5, 5A and 5B. Subsequent photolithographic processes will embed the carriers 40 between polymer electrodes. Microstamping is one exemplary process using a laser to engrave the sheet 200 with a patterned shape of the tape spring-type carrier.

Thermoplastic nanoimprint lithography (T-NIL) is another suitable process. Thermoplastic nanoimprint lithography uses a thin layer of imprint resist thermoplastic polymer spun-coated onto a substrate (not shown). Then the substrate, which has topological patterns of the tape spring shape, is brought into contact with the polymeric sheet 200 and the mold and sheet are pressed together under pressure. When heated up above the glass transition temperature of the polymer sheet 200, the pattern on the mold is pressed into the softened polymer. After cooling, the mold is separated from the sheet 200 and the tape spring pattern resist is left on the sheet 200. A pattern transfer process (reactive ion etching, normally) is used to transfer the pattern in the resist to the underneath sheet 200.

Alternatively, cold welding between two metal surfaces can be used to transfer low-dimensional nanostructured metal without heating (especially for critical sizes less than ~10 nm) onto sheet 200. Because the cold welding approach does not require heating, it has the advantage of reducing surface contact contamination or defect due normally attendant heating-related processes.

Other methods for shaping metal into a concave/convex structure suitable for manufacturing a tape spring-type carrier according to the present invention include fluting, extrusion, and electrostatic discharge micromachining (ESD).

The plurality of thusly produced tape spring-type carriers 40 connected to a manifold 44 (four shown carrier are shown in the subassembly designated 204 in FIG. 18A) are built into neural probes 16 according to one of the exemplary structures shown in FIGS. 5, 5A and 5B. The manifolds 40 are similar to those depicted in FIG. 2.

The tape spring-type carrier 40 may further extend the functionality of the system 10 by providing fluidic channels through which therapeutic drugs, drugs to inhibit biologic response to the implant, or any other suitable fluid may be transmitted. This provides for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener or stylet may be inserted to aid with implantation. Alternatively, the carrier may further include a separate lumen through which the stiffener or stylet may be inserted.

Thus, a plurality of neural probes 16 constructed with a tape spring-type carrier 40 according to the present invention and deployed from an exemplary guide tube 12 increases the effective site area to allow increased charge injection while maintaining safe electrochemical and biological limits. This will enable, for example, precise current steering to selectively stimulate neural structures. The thusly deployed neural probes can be used to establish one or more tunable neural interface region for the device. Multiple neural interface regions can be overlapping or non-overlapping. Additionally, at least two electrode sites from each probe 16 may be grouped to form a larger composite site that enables tuning the neural interface region for recording and/or stimulation. This grouping of sites can be through intrinsic connection of the site traces, or it can be through external connections for real-time tuning.

While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. A neural intervention system, comprising:
a guide tube comprising a guide tube sidewall extending along a longitudinal axis from a proximal guide tube portion having a proximal guide tube end to a distal guide tube portion having a distal guide tube end, wherein a tube lumen extends from the proximal guide tube end to at least the distal guide tube end;
a plurality of deployment channels disposed inside the guide tube, each of the plurality of deployment channels comprising a channel sidewall defining a channel lumen extending from a proximal channel open end to a distal channel open end as an open port at the guide tube sidewall, wherein the proximal channel open end of a first deployment channel of the plurality of deployment channels resides at a first location along a first imaginary plane aligned substantially perpendicular to the longitudinal axis and wherein the proximal channel open end of a second deployment channel of the plurality of deployment channels resides at a second location along the first imaginary plane radially closer to the longitudinal axis;
an actuation mechanism having a length extending from a proximal actuation end to a distal actuation portion; and
a plurality of neural probes that is registered with the plurality of deployment channels and that is connected to a manifold attached to the distal actuation portion of the actuation mechanism, at least one neural probe extending from a proximal probe end to a distal probe portion having a distal probe end,
wherein the distal probe portion has at least one electrode configured for electrical stimulation of body tissue or recording of biological characteristics, and wherein at least the distal probe end is received in at least one deployment channel of the plurality of deployment channels; and
wherein the proximal probe end is connected to the distal actuation portion, the proximal actuation end is movable in a distal direction along the longitudinal axis to cause the at least one neural probe to move through the at least one deployment channel and out the distal channel open end to thereby move the at least one electrode into a body tissue.

2. The neural intervention system of claim 1 wherein the proximal channel open end of one of the channel lumens of one of the plurality of deployment channels resides along the first imaginary plane to the distal channel open end substantially forms an angle ranging from 10 degrees to 180 degrees with respect to the longitudinal axis.

3. The neural intervention system of claim 1 wherein the distal guide tube end is either pointed or curved.

4. The neural intervention system of claim 1 wherein the plurality of deployment channels comprises at least two deployment channels, each of the at least two deployment channels having its proximal channel open end residing along the first imaginary plane, but with a first one of the at least two deployment channels having its distal channel open end as a first open port at a more distal location along the guide tube sidewall than the distal channel open end of the other of the at least two deployment channels.

5. The neural intervention system of claim 1 wherein the open port formed in the guide tube sidewall by the distal channel open end has a rectangular cross-section or a tape spring-type shaped cross-section.

6. The neural intervention system of claim 1 wherein the neural probe is configured to extend outwardly in a substantially radial direction upon deployment from the at least one deployment channel and out the distal channel open end thereof.

7. The neural intervention system of claim 1 wherein at least two of the plurality of neural probes have different lengths from one another.

8. A neural intervention system, comprising:
a guide tube extending along a longitudinal axis, wherein a tube lumen extends through a portion of the guide tube;
a plurality of deployment channels disposed in a distal portion of the guide tube, each deployment channel extending from a proximal channel open end to a distal channel open end,
wherein the distal channel open end has a trajectory that is off-axis with respect to the longitudinal axis,
wherein the proximal channel open end of a first deployment channel of the plurality of deployment channels resides at a first location along an imaginary plane aligned substantially perpendicular to the longitudinal axis; and
wherein the proximal channel open end of a second deployment channel of the plurality of deployment channels resides at a second location along the imaginary plane that is radially closer to the longitudinal axis;
a plurality of neural probes extending from a plunger, each of the neural probes having at least one electrode configured for electrical stimulation of body tissue or recording of biological characteristics, wherein a first subset of the plurality of neural probes is coupled to a first manifold and a second subset of the plurality of neural probes is coupled to a second manifold; and
an actuation mechanism having a length extending from a proximal actuation end to the plunger, the actuation mechanism being is movable to cause a first neural probe of the plurality of neural probes to move through a corresponding deployment channel to insert the first neural probe into body tissue.

9. The neural intervention system of claim 8 wherein the proximal channel open end of the each of the plurality of deployment channels is disposed on a common imaginary plane.

10. The neural intervention system of claim 8 wherein the trajectory is determined by an angle with respect to the longitudinal axis and a rotational position around the longitudinal axis.

11. The neural intervention system of claim 10 wherein the angle is in a range from about 10 degrees to about 180 degrees with respect to the longitudinal axis.

12. The neural intervention system of claim 8 wherein the actuation mechanism is moveable along the longitudinal axis of the guide tube.

13. The neural intervention system of claim 8 wherein the distal channel open end of a first deployment channel of the plurality of deployment channels is disposed at a more distal location along the guide tube the distal channel open end of a second deployment channel of the plurality of deployment channels.

14. The neural intervention system of claim 8 wherein the distal channel open ends have a rectangular cross-section or a curved cross-section.

15. The neural intervention system of claim 8 wherein the plurality of neural probes includes at least two neural probes having different lengths from one another.

16. The neural intervention system of claim 8, wherein the first and second manifolds are configured to support the first and second subsets of the plurality of neural probes in concentric circles.

17. A neural intervention system, comprising:
a guide tube extending along a longitudinal axis, wherein a tube lumen extends through a portion of the guide tube;
a plurality of deployment channels disposed in a distal portion of the guide tube, each deployment channel extending from a proximal channel open end to a distal channel open end, wherein the distal channel open end has a trajectory that is off-axis with respect to the longitudinal axis;
a plurality of neural probes extending from a plunger, each of the neural probes having at least one electrode configured for electrical stimulation of body tissue or recording of biological characteristics,
wherein a first subset of the plurality of neural probes is coupled to a first manifold and a second subset of the plurality of neural probes is coupled to a second manifold; and
wherein the first and second manifolds are configured to support the first and second subsets of the plurality of neural probes in concentric circles; and
an actuation mechanism having a length extending from a proximal actuation end to the plunger, the actuation mechanism being is movable to cause a first neural probe of the plurality of neural probes to move through a corresponding deployment channel to insert the first neural probe into body tissue.

18. The neural intervention system of claim 17 wherein the proximal channel open end of a first deployment channel of the plurality of deployment channels resides at a first location along a first imaginary plane aligned substantially perpendicular to the longitudinal axis.

19. The neural intervention system of claim 18 wherein the proximal channel open end of a second deployment channel of the plurality of deployment channels resides at a second location along the first imaginary plane that is radially closer to the longitudinal axis.

20. The neural intervention system of claim 17 wherein a distal guide tube end of the guide tube is either pointed or curved.

* * * * *